US011021518B2

(12) United States Patent
Selsted et al.

(10) Patent No.: US 11,021,518 B2
(45) Date of Patent: Jun. 1, 2021

(54) THETA DEFENSIN ANALOGS

(71) Applicants: Michael E. Selsted, Pasadena, CA (US); Dat Q. Tran, Alhambra, CA (US); Justin B. Schaal, Orange, CA (US)

(72) Inventors: Michael E. Selsted, Pasadena, CA (US); Dat Q. Tran, Alhambra, CA (US); Justin B. Schaal, Orange, CA (US)

(73) Assignee: The University of Southern California, Los Angeles, CA (US)

(*) Notice: Subject to any disclaimer, the term of this patent is extended or adjusted under 35 U.S.C. 154(b) by 0 days.

(21) Appl. No.: 16/914,038

(22) Filed: Jun. 26, 2020

(65) Prior Publication Data

US 2020/0407400 A1 Dec. 31, 2020

Related U.S. Application Data

(60) Provisional application No. 62/867,000, filed on Jun. 26, 2019.

(51) Int. Cl.
*C07K 7/64* (2006.01)
*A61P 31/00* (2006.01)
*A61K 38/00* (2006.01)

(52) U.S. Cl.
CPC .......... *C07K 7/64* (2013.01); *A61P 31/00* (2018.01); *A61K 38/00* (2013.01)

(58) Field of Classification Search
CPC .......... C07K 7/64; A61P 31/00; A61K 38/00
See application file for complete search history.

(56) References Cited

U.S. PATENT DOCUMENTS

| | | | |
|---|---|---|---|
| 7,119,070 | B2 | 10/2006 | Selsted et al. |
| 7,521,535 | B2 | 4/2009 | Zhang |
| 9,394,561 | B2 | 7/2016 | Barber |
| 10,512,669 | B2 | 12/2019 | Selsted |
| 10,589,039 | B2 | 3/2020 | DeHaan |
| 2003/0022829 | A1 | 1/2003 | Maury |
| 2008/0255052 | A1 | 10/2008 | Selsted et al. |
| 2009/0324562 | A1 | 12/2009 | Fagan |
| 2013/0157964 | A1* | 6/2013 | Selsted .............. A61P 1/04 514/21.1 |
| 2016/0263235 | A1 | 9/2016 | Castaigne |

FOREIGN PATENT DOCUMENTS

| | | | |
|---|---|---|---|
| EP | 2990415 | 3/2016 | |
| EP | 3105322 | 12/2018 | |
| KR | 20140053911 A | 5/2014 | |
| WO | WO-9921879 A1 * | 5/1999 | ............... C07K 7/64 |
| WO | 0068265 A1 | 11/2000 | |
| WO | 03105883 A1 | 12/2003 | |
| WO | 2007/044998 | 4/2007 | |
| WO | 2016023896 | 2/2016 | |

OTHER PUBLICATIONS

Conibear A.C., et al., "The Chemistry and Biology of Theta Defensins," Angewandte Chemistry International Edition, 2014, vol. 53, pp. 10612-10623.
Conibear A.C., et al., "The Cyclic Cystine Ladder in Θ- Defensins Is Important for Structure and Stability, but not Antibacterial Activity," The Journal of Biological Chemistry, Apr. 12, 2013, vol. 288 (15), pp. 10830-10840.
Doss M., et al., "Hapivirins and Diprovirins: Novel Θ-Defensin Analogs with Potent Activity against Influenza A Virus," The Journal of Immunology, Feb. 2012, vol. 188 (6), pp. 2759-2768.
International Search Report and Written Opinion for Application No. PCT/US2020/039865 dated Oct. 14, 2020, 13 pages.
International Search Report and Written Opinion for Application No. PCT/US2020/039945 dated Oct. 13, 2020, 13 pages.
Lehrer R.I., et al., "Θ-Defensins: Cyclic Peptides with Endless Potential," The Journal of Biological Chemistry, Aug. 3, 2012, vol. 287 (32), pp. 27014-27019.
Schaal J.B., et al., "Rhesus Macaque Theta Defensins Suppress Inflammatory Cytokines and Enhance Survival in Mouse Models of Bacteremic Sepsis," PLOS One, Dec. 2012, vol. 7 (12), Article e51337, pp. 1-11.

* cited by examiner

*Primary Examiner* — Sudhakar Katakam
(74) *Attorney, Agent, or Firm* — Fish IP Law, LLP

(57) ABSTRACT

Novel peptide analogs of a θ-defensin have been developed that provide a biphasic effect in treating infection and/or sepsis. These analogs are active at concentrations below those needed to provide a bactericidal or bacteriostatic effect, and function by initially recruiting effector cells of the immune system to address the infective organism followed by regulation of the immune system to down regulate the inflammatory response characteristic of sepsis and septic shock. These novel θ-defensin analogs are protective at concentrations where naturally occurring θ-defensins have no apparent effect, and include a core set of structural and sequence features not found in native θ-defensin.

16 Claims, 5 Drawing Sheets

Specification includes a Sequence Listing.

ized analogs of a β-defensin that show improved antibiotic effectiveness
THETA DEFENSIN ANALOGS This application claims the benefit of U.S. Provisional Patent Application No. 62/867,000 filed on Jun. 26, 2019. This and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

This invention was made with government support under Grant Nos. R01 AI125141 and R44 AR068833, awarded by the National Institutes of Health (NIH). The government has certain rights in the invention.

FIELD OF THE INVENTION

The field of the invention is biomedicine, specifically peptide drugs.

BACKGROUND

The background description includes information that may be useful in understanding the present invention. It is not an admission that any of the information provided herein is prior art or relevant to the presently claimed invention, or that any publication specifically or implicitly referenced is prior art.

Under some circumstances the body's protective inflammatory response can result in injury or even death. For example, sepsis or septic shock is a result of an inflammatory immune response. Treatment of septic shock is primarily by the administration of antibiotics and provision of supportive care and vasopressive drugs to stabilize blood pressure. Morbidity, however, remains significant. Death rates from such inflammatory responses range from about 30% for sepsis to about 80% for septic shock. Accordingly, there is significant interest identifying therapeutic compounds that are effective in treating various aspects of sepsis and of septic shock.

Defensins are a diverse family of small antimicrobial proteins that are part of the body's nonspecific defense against infection. There are three different and structurally distinct classes of defensin proteins: alpha, beta, and theta defensins. The α and β defensins are linear, tri-disulfide containing peptides having molecular weights of about 2.6 kDa or 4.5 kDa, respectively. In contrast, θ-defensins are cyclic peptides (i.e. circular peptides wherein the backbone is formed by sequential peptide bonds with neither a free amino or carboxyl terminus) composed of 18 amino acids.

θ-defensins are expressed in tissues of rhesus monkeys, baboons, and other Old World monkeys. They are not present in humans and other hominids. Naturally occurring θ-defensins are composed of 18 backbone cyclized (i.e. through the alpha-amine groups rather than side chain moieties) peptides stabilized by three disulfide bonds. These three disulfide bonds are conserved among all known θ-defensins. θ-defensins were originally discovered and classified as defensins based on the antimicrobial properties of the peptides. More recently it has been found that θ-defensins can have potent immunomodulatory effects.

International Patent Application Publication No. WO 2007/044998 (to Leherer et al) describes relationships between structure and biological activity for retrocyclin peptides and analogs of such peptides that include varying degrees enantiomer content in an attempt to derive structure/activity relationships. These analogs, however, retain the length and structure of the native retrocyclin. In addition, the reference is only instructive for antibacterial activity.

Peptide analogs of various defensins have been investigated. For example, European Patent Application EP2990415 (to Colavita et al) describes circularized analogs of a β-defensin that show improved antibiotic effectiveness relative to the parent protein. Such β-defensins, however, have been shown to stimulate release of pro-inflammatory cytokines, which raises safety concerns and limits their utility.

United States Patent Application Publication No. US 2003/0022829 (to Maury et al) describes synthesis and biologic activity of chimeric θ-defensins and speculates on the possibility of making conservative amino acid substitutions, however these appear to retain the length and structure of native θ-defensins. U.S. Pat. No. 10,512,669 (to Selsted et al) describes several tetradecapeptide θ-defensin analogs derived from RTD-1, and their biological properties.

There remains, therefore, a need for safe and effective compounds for the management and/or treatment of sepsis/septic shock and the physiologically related disorders resulting from dysregulated inflammatory reactions.

SUMMARY OF THE INVENTION

The inventive subject matter provides synthetic analogs of θ-defensins that have improved activity in treating sepsis and/or septic shock relative to native θ-defensins, at concentrations that are below those at which the analogs have direct bactericidal and/or bacteriostatic effect.

One embodiment of the inventive concept is a cyclic peptide consisting of 14 amino acids and having a structure as shown in FIG. 2A, which includes two disulfide bonds between two pairs of cysteines. In such a peptide AA3 and AA12 are cysteines joined by a disulfide bond, AA5 and AA10 are cysteines joined by a disulfide bond, AA4 is a first hydrophobic amino acid, AA11 is a second hydrophobic acid, AA6 is arginine, AA7 is arginine, AA8 is arginine. The cyclic peptide has a total of four arginine residues that provide a positive charge content of about 28% at physiological pH. The first hydrophobic amino acid and the second hydrophobic amino acid can be leucine or isoleucine. AA1 can be glycine. AA2 can be a third hydrophobic amino acid, such as valine or phenylalanine. AA9 can be a fourth hydrophobic amino acid, such as valine or phenylalanine. AA13 can be glycine. AA14 can be arginine. In some embodiments AA4 cannot be alanine or serine. In some embodiments AA11 cannot be alanine or serine. In some embodiments the cyclic peptide is MTD12813 (SEQ ID NO. 2).

Such a cyclic peptide can be an analog of a θ-defensin that provides improved survival when applied systemically in a murine sepsis model relative to the θ-defensin itself. In some embodiments the cyclic peptide provides a biphasic response on application to a murine model of sepsis. Such a biphasic response includes a first phase of recruitment of host effector cells having antimicrobial activity and a second phase of moderation of host inflammatory response. In some embodiments the cyclic peptide has a TACE inhibiting activity, and/or suppresses at least one of expression, processing, and release of TNF.

Such a cyclic peptide retains activity following exposure to environmental extremes of temperature, low pH, freezing and/or thawing, and dissolution in a biological matrix (such as blood, plasma, or serum. In some embodiments such a cyclic peptide is non-immunogenic at doses effective to treat or prevent sepsis and/or septic shock. Such cyclic peptides can activate a host immune system to enhance host clearance of pathogens, and can also have an activity that modulates inflammation to enhance disease resolution and survival at doses effective to treat or prevent septic shock.

Another embodiment of the inventive concept is a method of treating or preventing septic shock by administering a cyclic peptide as described above to an animal at risk of septic shock.

Another embodiment of the inventive concept is the use of a cyclic peptide as described above in treating or preventing sepsis and/or septic shock, or the use of such a cyclic peptide in preparing a medicament that is effective in treating or preventing septic shock.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 shows a schematic depiction of exemplary cyclic peptides referred to throughout. RTD-1 (SEQ ID NO. 1) is a naturally occurring octadecapeptide θ-defensin. Remaining peptides are θ-defensins analogs.

FIG. 2A shows a schematic of a cyclic defensin analog, showing numeric designations for amino acids by position along the cyclic chain. FIG. 2B provides an example of the application of these designations to amino acids of the MTD12813 (SEQ ID NO. 2) peptide.

DETAILED DESCRIPTION

Figure 1:
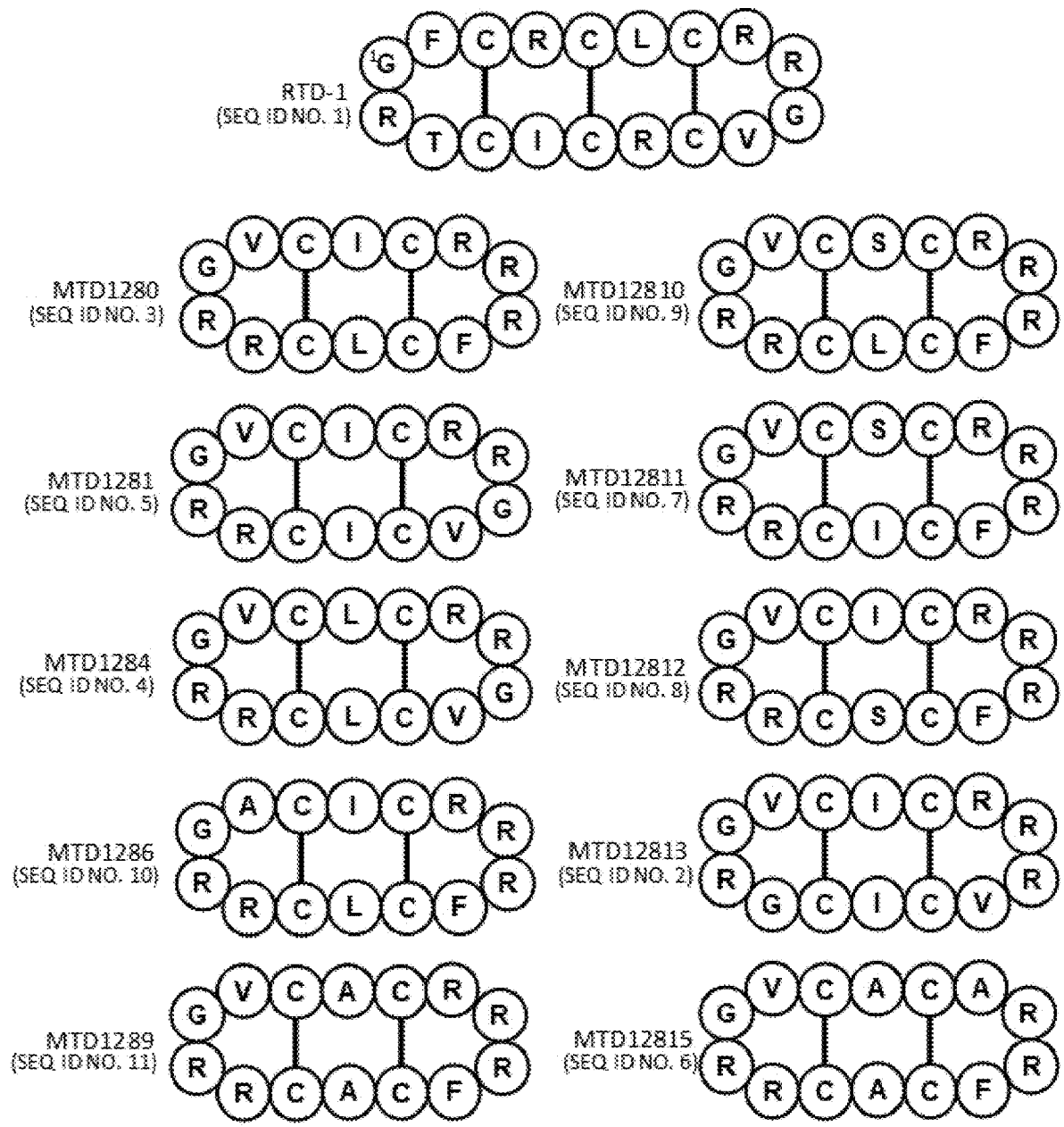
FIG. 1.

The inventive subject matter provides novel peptides that induce a biphasic effect in treating infection and/or sepsis, by initially recruiting effector cells of the immune system to address the infective organism followed by regulation of the immune system to prevent a systemic inflammatory response as found in sepsis and septic shock. The novel peptides are analogs of naturally occurring θ-defensins with sequences that have been modified to provide an indirect antimicrobial effect via recruitment of effector cells of the host immune system and to prevent and/or treat sepsis/septic shock. These novel θ-defensin analogs are effective at subantimicrobial plasma concentrations that do not provide a direct anti-microbial effect (i.e. that do not generate a bactericidal or a bacteriostatic effect) in the absence of host innate immune effectors. Such θ-defensin analogs are protective at concentrations where native θ-defensins have no apparent effect, and include a core set of structural and sequence features not found in native θ-defensins.

Within the context of this application, a "subantimicrobial" concentration in regard to a should be understood to be a concentration at which the compound so described has no antimicrobial effect when applied to the a representative microbial pathogen in vitro (e.g. in a liquid culture medium), e.g. in the absence of host immune effectors For example, a subantimicrobial concentration of a compound in regard to *Klebsiella pneumoniae* would be a concentration that is less than that which demonstrates an antimicrobial effect against the organism in an in vitro setting (e.g. in the absence of host immune effectors). Such subantimicrobial concentrations can be determined experimentally (for example, by culture from a patient sample) or, preferably, from historical data.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

One should appreciate that the disclosed peptides provide many advantageous technical effects, including provision of a biphasic response that is effective in reducing mortality from sepsis/septic shock when administered in low, subantimicrobial amounts.

Inventors have described synthetic cyclic tetradecapeptide analogs of the theta defensin RTD-1 that showed some of the activities of the parent peptide, despite their smaller size and reduced number of disulfide bonds. The structures of natural theta defensin RTD-1 (SEQ ID NO. 1) and some exemplary synthetic cyclic tetradecapeptide analogs are shown in FIG. 1. As shown, RTD-1 (which is expressed naturally in rhesus monkeys) is a cyclic octadecapeptide that includes 3 pairs of cysteines coupled by disulfide bonds that transit the circular primary structure of the peptide. A number of examples of synthetic (i.e. non-naturally occurring) analogs of RTD-1 are shown. Each of the exemplary synthetic analogs is a tetradecapeptide that includes 2 pairs of cysteines coupled by disulfide bonds. These disulfide bonds transit the circular primary structure of the synthetic peptides to form a "box" substructure that incorporates additional amino acids. It should be appreciated that these exemplary analogs show varying degrees of sequence identity with RTD-1, and in some instances show conservative amino acid substitutions near and between the "box" defined by cysteines of the synthetic peptide analogs.

Inventors have prepared and screened a series of θ-defensin analogs based on the analog designated MTD1280 (see FIG. 1, SEQ ID NO. 3) a synthetic peptide that provides substantially improved effects (relative to RTD-1) in long term survival of mice in a model of sepsis, and that provides these effects at surprisingly low concentrations. It should be appreciated that long term survival of sepsis requires both management of the infecting organism and of the shock induced by the host response to the infection, either of which can lead to death.

While examples of activity against sepsis and/or septic shock are provided, Inventors believe that θ-defensin analogs as described herein can be effective at treating a variety of conditions resulting from dysregulation of the immune or inflammatory response, including chronic conditions. Examples of such chronic conditions include rheumatoid arthritis and inflammatory bowel disease.

The Inventors note that θ-defensins have been found to have antiviral activity, and believe that θ-defensin analogs of the inventive concept can similarly provide anti-viral activity, and can prove useful in treating viral disease and inflammatory sequelae of viral infection. Such treatment includes prophylaxis and/or active disease. In some embodiments active disease so treated is symptomatic. In other embodiments active disease so treated is asymptomatic.

Surprisingly, θ-defensin analogs were identified that provide a biphasic response in modulating the immune system. The initial effect is opsonic, recruiting effector cells to the sepsis site. This serves to combat infection, and surprisingly was found to occur at concentrations of the θ-defensin analog that demonstrated neither a bactericidal nor a bacteriostatic effect (i.e. subantimicrobial concentrations). Following this initial opsonic effect these synthetic θ-defensin analogs exhibit a longer term immunomodulatory effect (for example, reducing TNF, IL-6 and other inflammatory cytokines) that contributes to long term survival in preventing septic shock.

Figure 2A:
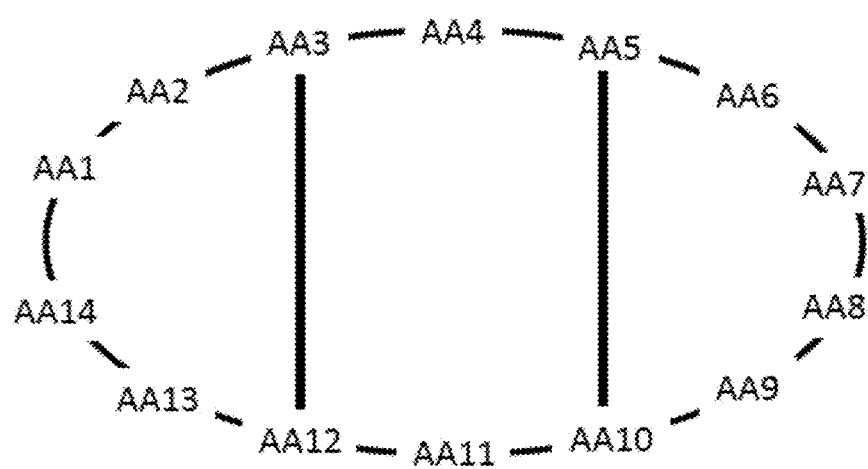
FIGS. 2A and 2B.
Figure 2B:
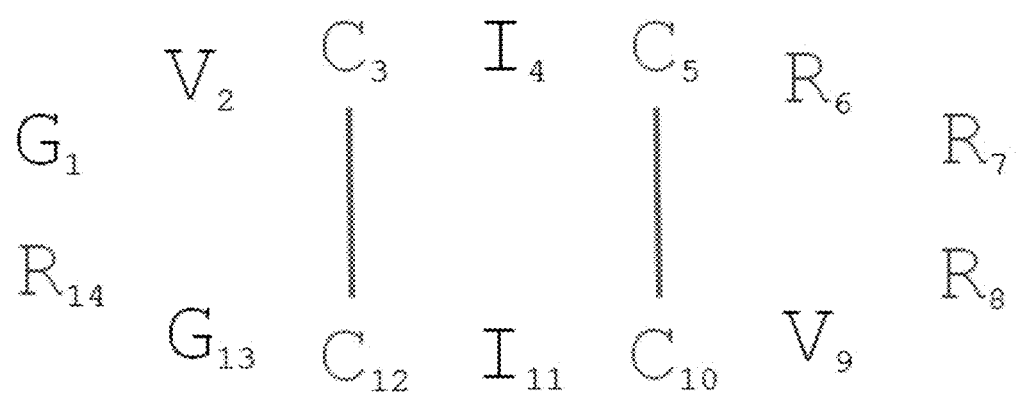

As noted above, examples of a naturally occurring θ-defensin and exemplary θ-defensin analogs are shown in FIG. 1. It should be appreciated that these are cyclic peptides that lack conventional amino- and carboxyl-termini; as such amino acid sequence information as provided in accompanying amino acid sequence listings should not be construed as based on a discrete N-terminus or C-terminus. The primary structure of the naturally occurring θ-defensin RTD-1 (SEQ ID NO. 1) is shown at the top of FIG. 1. The remaining peptides are exemplary non-natural analogs of θ-defensins. In the 14-amino acid analog series, it should be appreciated their three dimensional structures include a first β-turn formed by amino acids 6 to 9 and a second β-turn formed by amino acids 13, 14, 1, and 2 as designated using a numbering system adapted for use with cyclic θ-defensins and their analogs and as shown in FIGS. 2A and 2B.

Although these cyclic peptides do not have free amino- or carboxyl-termini, amino acid positions within the cyclic structure can be designated based on their positions relative to certain structural features (such as disulfide bonds and/or a distinctive 'triplet' of arginines). Such a set of designations as utilized for this purpose within this application is illustrated in FIG. 2A, where amino acids are designated 1 to 14 (AA1, AA2, etc.) in a cyclic teradecapeptide structure having a circular and continuous chain of peptide bonds through the primary amines of the individual amino acids (i.e. not through side chain groups), and in which two intra-peptide covalent bonds occur between side chains of cysteine amino acids designated AA3 and AA12 and between side chains of cysteine amino acids designated amino acids AA5 and AA10. FIG. 2B depicts application of amino acid positions as within the context of this application, as applied to an exemplary synthetic cyclic tetradecapeptide (MTD12813 peptide, SEQ ID NO. 2). Amino acid identity is designated using single-letter amino acid code.

Figure 3:
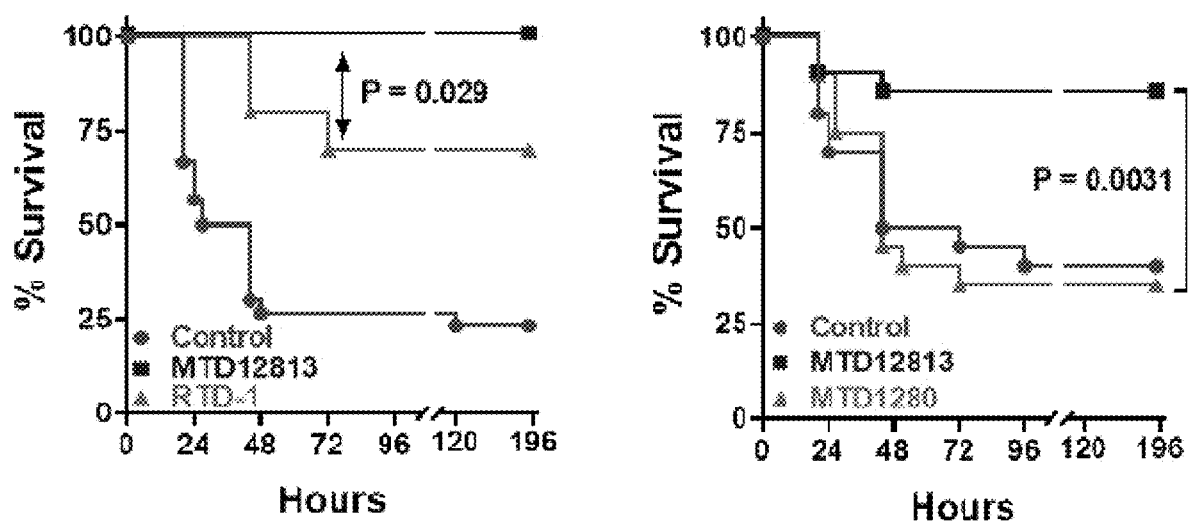
FIG. 3: Shows the results of efficacy studies of macrocyclic peptides in a murine carbapenem resistant *Klebsiella pneumoniae* sepsis model.

FIG. 3 shows the results of application of RTD-1 (SEQ ID NO. 1) and exemplary novel synthetic tetradecapeptides in a murine model of sepsis utilizing an antibiotic-resistant bacteria that results in 75% mortality (i.e. 25% survival) if untreated. BALB/c mice were infected interperitoneally with $3-5 \times 10^8$ CFU of a carbapenem resistant strain of *Klebsiella pneumoniae* (KPC+-Kp BAA-1705 (ATCC)) and treated with peptide one hour post infection. The left panel of FIG. 3 shows exemplary results of comparative studies between the synthetic peptide MTD12813 (SEQ ID NO. 2) and naturally occurring RTD-1 administered at 5 mg/kg. The right panel of FIG. 3 shows exemplary results of comparative studies between the synthetic peptides MTD12813 and MTD1280 (SEQ ID NO. 3) administered at 0.5 mg/kg. P-values were determined by Fisher's exact test. The therapeutic peptides were provided intraperitoneally 1 hour after induction of sepsis.

As shown in the left panel of FIG. 3, at 5 mg/kg RTD-1 (SEQ ID NO. 1) provides only partial protection (70% survival vs 25% for sham controls), whereas MTD12813 (SEQ ID NO. 2) provides complete protection from sepsis and septic shock. As shown in the right panel of FIG. 3, at 0.5 mg/kg the effects of MTD1280 (SEQ ID NO. 3) on survival are essentially identical to that of the sham control, whereas MTD12813 provides almost 90% survival. This difference is highly significant ($P=0.0031$).

It should be appreciated that at these dosages a θ-defensin and/or its analog does not produce a drug Cmax sufficient to have an appreciable direct antimicrobial (e.g. bactericidal, bacteriostatic) effect. Without wishing to be bound by theory, Inventors believe that the antimicrobial effects of MTD12813 (SEQ ID NO. 2) characteristic of the first phase of the biphasic response are the result of a systemic immune activating mechanisms that result in recruitment and stimulation of cells from the host immune system, which in turn phagocytose, kill, and clear the pathogen. In addition, MTD12813 moderates the inflammatory response to mitigate deleterious effects of hyperactivated and/or unresolved systemic inflammation, such as cytokine storm.

Figure 4:
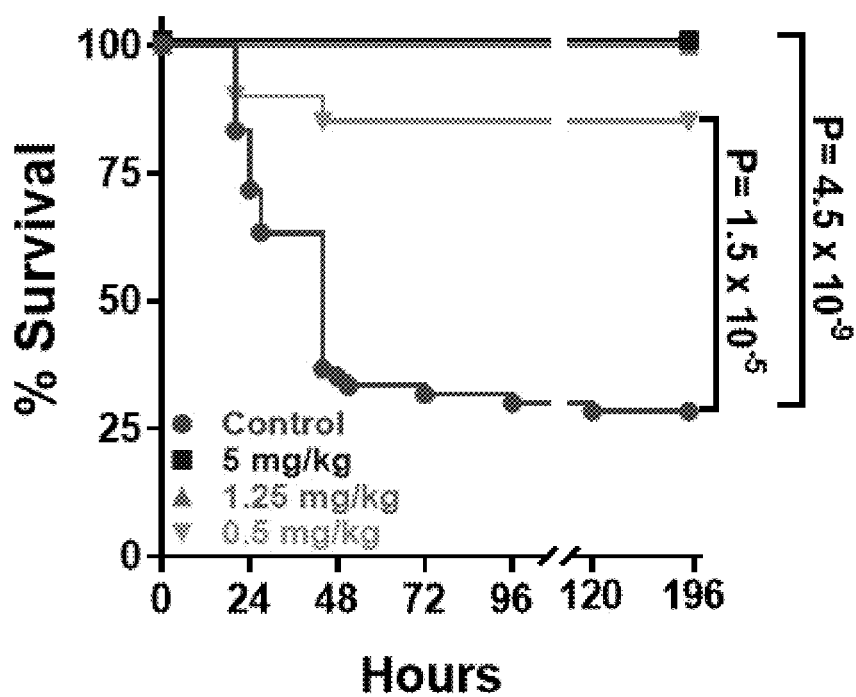
FIG. 4: Shows the results of potency studies of MTD12813 (SEQ ID NO. 2) in a murine carbapenem resistant *Klebsiella pneumoniae* sepsis model.

FIG. 4 shows typical results for survival studies in such a murine survival study for various concentrations of MTD12813 (SEQ ID NO. 2), utilizing the same murine sepsis model as used in studies shown in FIG. 3. BALB/c mice were infected i.p. with KPC+-Kp BAA-1705 (ATCC) and treated with a single dose of MTD12813, at the levels indicated, 1 hour post infection. The significance (P-values determined by Fisher's exact test) of the therapeutic effect for each dose is shown. As shown, 1.25 mg/kg of this novel θ-defensin analog is as effective as 5 mg/kg, and a dose of MTD12813 as low as 0.5 mg/kg is also highly effective. It should be appreciated that 0.5 mg/kg is the lowest dose tested, and that Inventors believe that MTD12813 is effective at still lower doses, for example down to 0.25 mg/kg, 100 mg/kg, 50 mg/kg, 25 mg/kg, or 10 µg/kg.

As noted above, MTD12813 (SEQ ID NO. 2) was identified in screening studies of a range of cyclic peptide analogs of the θ-defensin RTD-1 (SEQ ID NO. 1). RTD-1 is a cationic, arginine-rich cyclic peptide that includes 18 amino acids and 3 disulfide bonds between pairs of cysteines (FIG. 1). Other active θ-defensin analogs are also shown in FIG. 1.

Inventors have identified a number of novel θ-defensin analogs that show superior performance relative to MTD1280 (SEQ ID NO. 3), despite having similar covalent structures (e.g. length, cyclic configuration, two pairs of disulfide bonds, and cationic character). Features evaluated included survival efficacy in antibiotic resistant *K. pneumoniae* sepsis, biocompatibility (lack of toxicity), in vitro suppression of TNF-α (TNF) release, and inhibition of TACE. Amino acid sequences of exemplary cyclic peptides are shown in Table 1. It should be appreciated that amino acids identities are indicated using the numerical designation for corresponding positions within the cyclic structures as established in FIG. 2. Properties and activities associated with these peptides are shown in Table 2

A number of sequence features were identified that confer superior activity to RTD-1- and MTD1280-derived analogs compared to these reference peptides. All active θ-defensin analogs can have at least:
  Two disulfide bonds, between Cys3 and Cys12 and between Cys5 and Cys10, respectively.
  A hydrophobic amino acid positioned between Cys3 and Cys5 and a hydrophobic amino acid positioned between Cys10 and Cys12 in the primary structure of the θ-defensin analog (i.e. at positions 4 and 11), preferably leucine or isoleucine. In combination with the disulfide bonds noted above this defines a feature referred to as the "C-X-C box" within the circular primary structure of the peptide, where "C" is a cysteine and "X" is preferably either leucine or isoleucine.
  In some embodiments, a C-X-C box that includes arginine.
  A total of four arginine residues that provide the peptide with a charge of +4 at physiological pH.
  A triplet of adjacent arginines at positions 6, 7, and 8, i.e. within the first β-turn.
In some embodiments active θ-defensin analogs can also include one or more of the following features:
  A glycine at position 1 and a glycine at position 13.
  Hydrophobic amino acids at position 2 and position 9, preferably valine or phenylalanine.

TABLE 1

Amino acid positions are designated according to the convention shown in FIG. 2A.

| Analog name | 1st β turn | | | | | | | | | 2nd β turn | | | | SEQ ID NO. |
|---|---|---|---|---|---|---|---|---|---|---|---|---|---|---|
| | 3 | 4 | 5 | 6 | 7 | 8 | 9 | 10 | 11 | 12 | 13 | 14 | 1 | 2 | |
| MTD12813 | C | I | C | R | R | R | V | C | I | C | G | R | G | V | 2 |
| MTD1280 | C | I | C | R | R | R | F | C | L | C | R | R | G | V | 3 |
| MTD1284 | C | L | C | R | R | G | V | C | L | C | R | R | G | V | 4 |
| MTD1281 | C | I | C | R | R | G | V | C | I | C | R | R | G | V | 5 |
| MTD12815 | C | A | C | A | R | R | F | C | A | C | R | R | G | V | 6 |
| MTD12811 | C | S | C | R | R | R | F | C | I | C | R | R | G | V | 7 |
| MTD12812 | C | I | C | R | R | R | F | C | S | C | R | R | G | V | 8 |
| MTD12810 | C | S | C | R | R | R | F | C | L | C | R | R | G | V | 9 |
| MTD1286 | C | I | C | R | R | R | F | C | L | C | R | R | G | A | 10 |
| MTD1289 | C | A | C | R | R | R | F | C | A | C | R | R | G | V | 11 |

TABLE 2

Properties and activities of cyclic peptide analogs of the θ-defensin RTD-1 as listed in Table 1.

| Analog name | Positive charge | Molecular Weight | Kp sepsis % survival at 5 mg/kg | TACE IC$_{50}$ µg/mL | TNF % suppression at 5 mg/kg |
|---|---|---|---|---|---|
| MTD12813 | 4 | 1572 | 100 | 0.858 | 95.6 |
| MTD1280 | 5 | 1720 | 80-100 | 2.202 | 98.7 |
| MTD1284 | 4 | 1572 | 53.3 | 1.150 | 78.8 |
| MTD1281 | 4 | 1572 | 40 | 0.546 | 83.0 |
| MTD12815 | 4 | 1550 | toxic | 1.828 | not tested |
| MTD12811 | 5 | 1693 | 30 | 3.192 | 37.5 |
| MTD12812 | 5 | 1693 | 20 | 1.869 | 14.9 |
| MTD12810 | 5 | 1693 | 0 | 2.613 | 2.0 |
| MTD1286 | 5 | 1691 | toxic | 0.515 | not tested |
| MTD1289 | 5 | 1635 | toxic | 2.737 | not tested |

An arginine within the second β-turn (e.g. at position 14).

Toxicity of candidate peptides suggests that active θ-defensin analogs should not include one or more of:
  An alanine at position 4.
  An alanine at position 11.

Accordingly, Inventors believe a θ-defensin analog that include a "C-X-C box" structure as described above, a triplet of adjacent arginine residues at positions 6, 7, and 8, a hydrophobic amino acid (e.g. valine or phenylalanine) at position 9, and having a net positive charge of +4 (about 28% of total amino acid content) due to arginine content will be effective in reducing mortality and/or improving long term survival in sepsis, and can be effective in treating other conditions characterized by dysregulation of an inflammatory or immune response.

Analogs of θ-defensins as described herein can be applied using any suitable method. For example, such analogs can be provided by injection or infusion. The high degree of effectiveness observed for some θ-defensin analogs indicates that these can be provided to an individual in need of treatment in effective amounts by simple subcutaneous, intradermal, subdermal, intravenous, and/or intramuscular injection.

Alternatively, the low molecular weight and high degree of stability conferred by circular structure and the presence of disulfide bonds can allow for oral administration of θ-defensin analogs of the inventive concept. Such oral administration can include administration of a solution or suspension of the θ-defensin analog in a liquid pharmaceutical carrier suitable for oral administration. In some embodiments a θ-defensin analog can be provided in a dry or lyophilized form that is reconstitute in a liquid media prior to oral administration. Such dry or lyophilized formulations can include a stabilizer. Suitable stabilizers include carbohydrates (e,g, mannitol, sucrose, trehalose) and/or proteins (e.g. albumin).

Alternatively, analogs of θ-defensin can be provided in a tablet, capsule, pill, or other suitable solid and compact form for oral administration. Such formulations can include coatings, shells, or similar components that provide for delayed release of the θ-defensin analog (for example, delaying release until reaching the small intestine). Such formulations can include the θ-defensin in liquid form within an enclosure or coating. Alternatively such formulations can include a θ-defensin analog in a dry or lyophilized form. Suitable dry or lyophilized forms include powders, granules, and compressed solids. Such dry or lyophilized formulations can include a stabilizer. Suitable stabilizers include carbohydrates (e,g, mannitol, sucrose, trehalose) and/or proteins (e.g. albumin).

As noted above, θ-defensin analogs of the inventive concept can effectively treat sepsis and/or septic shock. In some embodiments such treatment is in response to an ongoing, acute condition. In other embodiments such treatment is prophylactic, for example used to prevent the development of septic shock when the individual is suspected of having sepsis or a high probability of developing sepsis. Treatment can be provided by administration of a θ-defensin analog of the inventive concept on any suitable schedule. For example, a θ-defensin analog can be provided as a single dose, periodic doses, or as a continuous infusion. Periodic doses can be administered at any suitable intervals. Suitable intervals can be hourly, every 2 hours, every 4 hours, 4 times a day, 3 times a day, twice a day, once daily, every 2 days, every 3 days, twice a week, weekly, every 2 weeks, every 4 weeks, every 2 months, every 3 months, every 4 months, 3 times a year, twice a year, or annually.

In some embodiments the mode of administration for a θ-defensin analog can be modified during the course of treatment. For example, a θ-defensin analog of the inventive concept can initially be administered by intravenous injection or infusion (e.g. to rapidly provide effective concentrations in acute sepsis or septic shock), followed by intradermal injection, intramuscular injection, and/or oral administration in order to maintain an effective concentration over a remaining period of treatment.

For prophylactic use, a θ-defensin analog can be administered prior to the onset of observable symptoms. For treatment of an active disease or condition a θ-defensin analog can be administered for a period of suitable to effectively treat the disease or condition. Such a period can be over for a controlled period of time, or can be long term (e.g. for treatment of chronic conditions).

In some embodiments of the inventive concept a θ-defensin analog can be used in combination with other pharmaceutically active compounds. Suitable compounds include a θ-defensin, a different θ-defensin analog, an antibacterial antibiotics, an antiviral, an antifungal antibiotic, an anti-inflammatory drug (e.g. steroids, non-steroidal anti-inflammatory drugs), a vasopressor, and/or a biologic (e.g. antibodies or antibody fragments). Such additional pharmaceutical compounds can be provided on the same schedule as the θ-defensin analog, or on an independent schedule. In some embodiments a θ-defensin analog-containing formulation can be provided that incorporates one or more of such additional pharmaceutically active compounds. Inventors believe that such cotherapy can provide a synergistic effect in which the cumulative effect of administration of the θ-defensin analog in combination with the additional pharmaceutically active compound exceeds the sum of the individual effects observed with treatment using the θ-defensin analog and the additional pharmaceutically active compound in amounts corresponding to those used for cotherapy.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A cyclic peptide consisting of 14 amino acids and having the following structure:

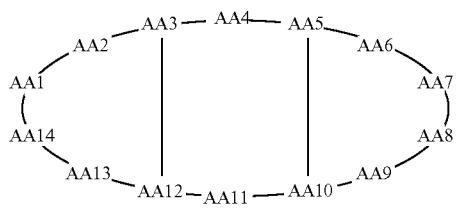

wherein AA1 is glycine, AA3 and AA12 are cysteines joined by a disulfide bond, AA5 and AA10 are cysteines joined by a disulfide bond, AA4 is a first hydrophobic amino acid, AA11 is a second hydrophobic acid, AA6 is arginine, AA7 is arginine, AA8 is arginine, and wherein the cyclic peptide has two glycines and has four arginine residues that provide a positively charged content of about 28% at physiological pH, and wherein AA2, AA9, AA13, and AA14 are amino acids.

2. The cyclic peptide of claim 1, wherein the first hydrophobic amino acid and the second hydrophobic amino acid are leucine or isoleucine.

3. The cyclic peptide of claim 1, wherein AA2 is a third hydrophobic amino acid.

4. The cyclic peptide of claim 1, wherein AA9 is a fourth hydrophobic amino acid.

5. The cyclic peptide of claim 1, wherein AA13 is glycine.

6. The cyclic peptide of claim 1, wherein AA14 is arginine.

7. The cyclic peptide of claim 1, wherein at least one of AA4 and AA11 is not alanine or serine.

8. The cyclic peptide of claim 1, wherein the cyclic peptide is MTD12813 (SEQ ID NO. 2).

9. A method of treating septic shock, comprising administering a cyclic peptide of claim 1 an animal at risk of septic shock.

10. The method of claim 9, wherein the cyclic peptide is an analog of a θ-defensin, and wherein the cyclic peptide provides improved survival when applied systemically in a murine sepsis model relative to the θ-defensin.

11. The method of claim 9, wherein the method provides a biphasic response on application to a murine model of sepsis, wherein the biphasic response comprises a first phase of recruitment of host effector cells having antimicrobial activity and a second phase of moderation of host inflammatory response.

12. The method of claim 9, wherein the method inhibits TACE activity.

13. The method of claim 9, wherein the method suppresses at least one of expression, processing, and release of a proinflammatory cytokine.

14. The method of claim 9, wherein the cyclic peptide retains activity following exposure to environmental extremes of temperature, low pH, freezing and/or thawing, and dissolution in a biological matrix.

15. The method of claim 9, wherein the cyclic peptide is non-immunogenic at doses effective to treat septic shock.

16. The method of claim 9, wherein the cyclic peptide activates a host immune system to enhance host clearance of pathogens.

* * * * *

SEQUENCE LISTING

<160> NUMBER OF SEQ ID NOS: 11

<210> SEQ ID NO 1
<211> LENGTH: 18
<212> TYPE: PRT
<213> ORGANISM: Macaca mulatta

```
<400> SEQUENCE: 1

Gly Phe Cys Arg Cys Leu Cys Arg Arg Gly Val Cys Arg Cys Ile Cys
1               5                   10                  15

Thr Arg

<210> SEQ ID NO 2
<211> LENGTH: 14
<212> TYPE: PRT
<213> ORGANISM: Artificial Sequence
<220> FEATURE:
<223> OTHER INFORMATION: Synthetic cyclic peptide MTD12813

<400> SEQUENCE: 2

Gly Val Cys Ile Cys Arg Arg Arg Val Cys Ile Cys Gly Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic cyclic peptide MTD1280

<400> SEQUENCE: 3

Gly Val Cys Ile Cys Arg Arg Arg Phe Cys Leu Cys Arg Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic cyclic peptide MTD1284

<400> SEQUENCE: 4

Gly Val Cys Leu Cys Arg Arg Gly Val Cys Leu Cys Arg Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic cyclic peptide MTD1281

<400> SEQUENCE: 5

Gly Val Cys Ile Cys Arg Arg Gly Val Cys Ile Cys Arg Arg
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic cyclic peptide MTD12815

<400> SEQUENCE: 6

Gly Val Cys Ala Cys Ala Arg Arg Phe Cys Ala Cys Arg Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic cyclic peptide MTD12811
```

```
<400> SEQUENCE: 7

Gly Val Cys Ser Cys Arg Arg Arg Phe Cys Ile Cys Arg Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic cyclic peptide MTD12812

<400> SEQUENCE: 8

Gly Val Cys Ile Cys Arg Arg Arg Phe Cys Ser Cys Arg Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic cyclic peptide MTD12810

<400> SEQUENCE: 9

Gly Val Cys Ser Cys Arg Arg Arg Phe Cys Leu Cys Arg Arg
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic cyclic peptide MTD1286

<400> SEQUENCE: 10

Gly Ala Cys Ile Cys Arg Arg Arg Phe Cys Leu Cys Arg Arg
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic cyclic peptide MTD1289

<400> SEQUENCE: 11

Gly Val Cys Ala Cys Arg Arg Arg Phe Cys Ala Cys Arg Arg
1               5                   10
```